United States Patent [19]

Scheler et al.

[11] Patent Number: 5,268,252
[45] Date of Patent: Dec. 7, 1993

[54] RADIATION-SENSITIVE ESTER AND PROCESS FOR ITS PREPARATION

[75] Inventors: Siegfried Scheler, Wiesbaden-Naurod; Wolfgang Zahn, Eltville; Axel Schmitt, Walluf; Gerhard Buhr, Koenigstein, all of Fed. Rep. of Germany

[73] Assignee: Hoechst Aktiengesellschaft, Frankfurt am Main, Fed. Rep. of Germany

[21] Appl. No.: 863,679

[22] Filed: Apr. 1, 1992

[30] Foreign Application Priority Data

Apr. 9, 1991 [DE] Fed. Rep. of Germany ....... 4111443

[51] Int. Cl.$^5$ ............................................. G03C 1/52
[52] U.S. Cl. .................................... 430/193; 430/190; 430/191; 430/192; 430/165; 430/166; 534/555; 534/557
[58] Field of Search ............... 430/190, 192, 193, 191, 430/165, 166; 534/555, 557

[56] References Cited

U.S. PATENT DOCUMENTS

| | | | |
|---|---|---|---|
| 4,404,272 | 9/1983 | Stahlhofen | 430/192 |
| 4,581,321 | 4/1986 | Stahlhofen | 430/325 |
| 4,732,836 | 3/1988 | Potvin et al. | 430/192 |
| 4,902,785 | 2/1990 | Potvin et al. | 534/557 |
| 5,035,976 | 7/1991 | Potvin et al. | 430/192 |
| 5,114,816 | 5/1992 | Scheler et al. | 430/192 |
| 5,162,510 | 11/1992 | Potvin et al. | 430/192 |

FOREIGN PATENT DOCUMENTS

| | | |
|---|---|---|
| 0212482 | 3/1987 | European Pat. Off. . |
| 0244763 | 11/1987 | European Pat. Off. . |
| 0369219 | 5/1990 | European Pat. Off. . |
| 3837500 | 5/1990 | Fed. Rep. of Germany . |

OTHER PUBLICATIONS

European Patent No. 0244762 (Nov. 1987) (abstract only).
German Patent No. 3325022 (Jan. 1985) (abstract only).
Trefonas et al. (1987) *SPIE: Advances in Resist Technology and Processing* IV 771: 194–210, describes the new principle for image enhancement in single layer positive photoresists.
Trefonas et al. (Aug. 1987) *Solid State Technology* 30: 131–137, describes photoresist design for submicron optical lithography application of polyphotolysis.
"Patent Abstracts of Japan", vol. 12, No. 235, (P-725)(3082), Jul. 6, 1988; and JP-A-63 027 835, published Feb. 5, 1988.

*Primary Examiner*—Charles L. Bowers, Jr.
*Assistant Examiner*—Geraldine Letscher
*Attorney, Agent, or Firm*—Foley & Lardner

[57] ABSTRACT

The invention relates to a radiation-sensitive ester which is the condensation product of (a) a compound containing 2 to 6 aromatic hydroxyl groups, (b) a ring-substituted (o-naphthoquinone 2-diazide)-4-sulfonic acid (compound $D_1$ and (c) an (o-naphthoquinone 2-diazide)-4- or -5-sulfonic acid which is not further substituted (compound $D_2$) and/or a non-radiation-sensitive organic acid (compound $D_0$), where the (b):(c) molar ratio is between 0.1:1 and 39:1.

22 Claims, No Drawings

RADIATION-SENSITIVE ESTER AND PROCESS FOR ITS PREPARATION

BACKGROUND OF THE INVENTION

The present invention relates to novel radiation-sensitive esters composed of a) a compound containing 2 to 6 aromatic hydroxyl groups, b) a ring-substituted (o-naphthoquinone 2-diazide)-4-sulfonic acid and c) an (o-naphthoquinone 2-diazide)-4- or -5-sulfonic acid which is not further substituted and/or a non-radiation-sensitive organic acid, and also to a process for their preparation.

The radiation-sensitive layer of standard copying materials is essentially composed of a mixture of an alkali-soluble cresol formaldehyde novolak with radiation-sensitive compounds, such as 1,2-benzo- or o-naphthoquinone 2-diazide derivatives. The novolak is soluble per se in aqueous alkaline solutions, but the radiation-sensitive o-quinone diazide compounds act as solution inhibitors. In the imagewise exposure of the layer to actinic radiation, the radiation-sensitive diazocarbonyl compound is converted into a carboxylic acid via a ketene intermediate. The carboxylic acid is readily soluble in aqueous alkaline solution and, consequently, also enhances the solubility of the novolak. The exposed regions of the copying layer dissolve in the alkaline developer solution, while the unexposed regions remain essentially unaltered and intact, with the result that a positive relief image of the master is produced on the layer support.

The solubility behavior described can, however, also be reversed. For this purpose, the recording layer is subjected to a heat treatment after imagewise irradiation. Under these circumstances, the resin molecules of the layer cross-link in the regions of the layer affected by the light. This process, referred to as "hardening" requires, as a rule, the presence of a "cross-linking agent" which brings about the cross-linking and, consequently, the hardening during the heat treatment, under the influence of the acid which has been produced from the o-quinone diazide during the exposure. During hardening heating is carried out to temperatures below the decomposition temperature of the o-quinone diazide. The heating can be carried out by irradiation, placement into a stream of hot gas, contact with heated surfaces, for example with heated rollers, or immersion in a heated bath of an inert liquid, for example water. The temperature is in general between 90° and 150° C., preferably between 100° and 130° C.

Efficient cross-linking agents are generally compounds which readily form a carbonium ion under the acid and temperature conditions described. Examples of these are the hexamethylolmelamine ethers in accordance with DE-A 33 25 022 (=U.S. Pat. No. 4,581,321) and also the compounds described in EP-A 0 212 482, such as 1,4-bishydroxymethylbenzene and 4,4'-bismethoxymethyl diphenyl ether, which contain two or more aromatically bound hydroxymethyl or alkoxymethyl groups. 2,6-Bishydroxymethyl-4-methylphenol in accordance with U.S. Pat. No. 4,404,272 is also known as a cross-linking agent.

After the heat treatment, the photoresist layer is, as a rule, subjected to a whole-surface exposure ("flood exposure") in order to render the still radiation-sensitive layer regions completely alkali-soluble. The flood exposure is in general carried out with the same light source which was also used for the image exposure.

The development following the flood exposure is in general carried out with one of the aqueous alkaline solutions which are also used to develop a positive-working photoresist. These are, for example, aqueous solutions of sodium hydroxide, tetramethylammonium hydroxide, trimethyl(hydroxyethyl)ammonium hydroxide, alkali-metal phosphates, alkali-metal silicates or alkali-metal carbonates, which solutions may contain wetting agents or fairly small amounts of organic solvents. During the development, the layer regions not affected by light in the original image exposure are washed out, with the result that a negative resist image of the master is obtained.

In most cases, the exposed and developed resist material is then treated with an etchant, in which process the etchant is only able to act on the layer support in the non-image regions. In this way, a negative etching image is produced on the layer support in the case of a positive-working copying layer and a positive etching image in the case of a negative-working copying layer.

The positive or negative relief image of the copying layer produced on the layer support by the processes described is suitable for various application purposes, inter alia as an exposure mask or as an image in the production of semiconductor components in microelectronics, as printing forms for letterpress, gravure or lithographic printing, and also for the production of nickel rotation cylinders in an electroplating process.

The commercial suitability of a copying layer, for example a photoresist layer, is assessed, inter alia, on the basis of the radiation sensitivity, the development and image contrast, the resolution and the adhesion to the layer support.

A high radiation sensitivity of the composition is an important factor in the manufacture of microelectronic circuits or components, especially in the so-called "in-line" processing of wafers, in which the throughput of wafers is determined by the longest lasting process step. With the relatively long exposure times hitherto necessary, the exposure equipment throughput is the limiting factor. The exposure equipment cycle times are too long, especially with monochromatic irradiation and with irradiation using shorter-wave actinic light, and this results in an unduly low production rate.

The resist resolution relates to the capability of a photoresist system to reproduce even the finest lines and gaps of a mask used for the exposure, the exposed and developed regions being required to exhibit a high degree of edge steepness and sharpness.

In many technical application fields, in particular in the production of semiconductor components in microelectronics, the photoresist has to achieve a particularly high resolution as very small line and gap widths (<1 μm) have to be reproduced. The ability to reproduce smallest details in the order of magnitude of 1 μm and less is of the greatest importance for the large-scale production of integrated circuits on silicon chips and similar components. If photographic processes are used, the integration density on such a chip can be increased by increasing the resolving power of the photoresist.

It is known that the resolution of a photoresist increases if photoactive compounds containing a plurality of radiation-sensitive radicals in one molecule are present in it since the radiation-sensitive component in the mixture is then increased. [P. Trefonas III and B. K. Daniels, "New Principle for Image Enhancement in Single Layer Positive Photoresists", SPIE Advances in Resist Technology and Processing IV, 771 (1987), 194–210; P. Trefonas III, B. K. Daniels and R. L. Fischer, "Photoresist Design for Submicron Optical Lithography: Application of Polyphotolysis"Solid State Technology 30 (1987), 131–137].

If the mixed esters mentioned in EP-A 0 244 762 and 0 244 763 are used, an improved resolution can already be observed. DE-A 38 37 500 reveals the superior properties of ring-substituted naphthoquinone diazide derivatives in lithographic applications. Esters of optionally substituted (o-naphthoquinone 2-diazide)-4- or -5-sulfonic acids with compounds which possess three or more aromatic hydroxyl groups often have, however, an unduly low solubility in the standard solvents, and this has the result that the resists prepared with these esters do not yet achieve adequate resolution.

SUMMARY OF THE INVENTION

Accordingly, it is an object of the present invention to provide novel compounds of substituted o-naphthoquinone 2-diazides and compounds containing two or more aromatic hydroxyl groups which have an increased solubility in the standard solvents and also in systems composed of solvents and binders (e.g., resins), as compared to known compounds.

Another object of the present invention is to provide a process for producing the foregoing compounds.

In accomplishing the foregoing objectives, there has been provided, in accordance with one aspect of the present invention, a radiation-sensitive ester which is the condensation product of (a) a compound containing two to six aromatic hydroxyl groups, (b) a compound D, which is a ring-substituted (o-naphthoquinone 2-diazide)-4-sulfonic acid, and (c) a compound selected from the group consisting of (i) a compound $D_2$ which is an (o-naphthoquinone 2-diazide)-4-sulfonic acid which is not further substituted or an (o-naphthoquinone 2-diazide)-5-sulfonic acid which is not further substituted and (ii) a compound $D_0$ which is a non-radiation-sensitive organic acid. The molar ratio (b):(c) (i.e., the molar ratio $D_1$:($D_2$ and/or $D_0$)) is between about 0.1:1 and 39:1.

In accordance with another aspect of the present invention there is provided a process for producing the foregoing radiation-sensitive ester which comprises the steps of condensing compound (a) in a polar organic solvent with a mixture of compounds (b) and (c) in the presence of a base, the molar ratio (b):(c) being between about 0.1:1 and 39:1, to form a condensation product, and isolating the condensation product.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

The present invention provides a radiation-sensitive ester which is composed of a) a compound containing two to six aromatic hydroxyl groups (referred to below as an aromatic polyhydroxyl compound),
b) a ring-substituted (o-naphthoquinone 2-diazide)-4-sulfonic acid (diazo compound $D_1$), and
c) an (o-naphthoquinone 2-diazide)-4- or -5-sulfonic acid which is not further substituted (diazo compound $D_2$) and/or a non-radiation-sensitive organic acid (compound $D_0$), where the $D_1$:($D_2$ and/or $D_0$) molar ratio is between about 0.1:1 and 39:1.

Suitable aromatic polyhydroxyl compounds are, in particular, compounds of the formula I

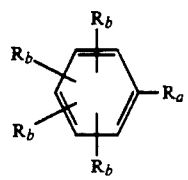

(I)

where $R_a$=—H, -X-$R_c$ or

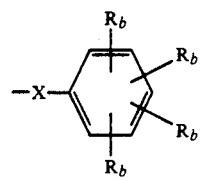

in which
$R_b$ is a hydrogen or halogen atom, or a hydroxyl or ($C_1$–$C_6$)alkyl group, with the proviso that at least two and not more than six of the $R_b$ groups are hydroxyl groups and the radicals $R_b$ are identical to, or different from, one another, X is a single bond, —O—, —S—, —$SO_2$—, —CO—, —CO—$CH_2$—, CO—$CH_2$—$CH_2$—, —CO—$CH_2$—CO—, —CO—$CH_2$—$CH_2$—CO—, —CO—O—, —CO—O—$CH_2$—, —CO—O—$CH_2$—$CH_2$—, —$CH_2$—CO—O—$CH_2$—, —$CH_2$—CO—O—$CH_2$—, —$CH_2$—, —$CH_2$—$CH_2$—, —$(CH_2)_3$—, —$C(CH_3)_2$—, —$C(CF_3)_2$—,

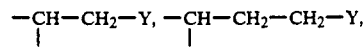

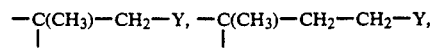

where $CH_2$ groups can be replaced by —O—, and hydrogen atoms by substituents such as alkyl or aryl, Y is a hydrogen atom or an alkoxy, carboxyl, alkoxycarbonyl, alkoxyalkoxycarbonyl or aryl group, the alkoxy, alkoxycarbonyl and alkoxyalkoxycarbonyl groups being optionally substituted by halogen or aryl and the aryl group being optionally substituted by alkyl, and $R_c$ is a hydrogen atom or an optionally halogen-substituted alkyl or aryl group.

Suitable polyhydroxyl compounds are, in addition, also compounds of the formula II

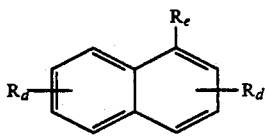

(II)

in which
R_c is a hydrogen atom or an optionally halogen- or alkyl-substituted 1-naphthylmethyl group

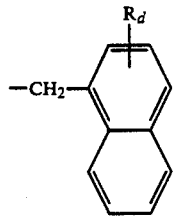

where
R_d is a hydrogen atom or a hydroxyl group, with the proviso that at least two of the R_d groups are hydroxyl groups.

Finally, suitable polyhydroxyl compounds are also those of the formula III

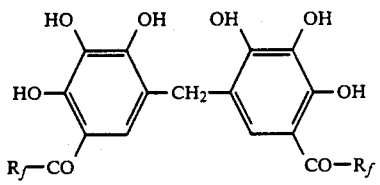

(III)

in which $R_f$ is a hydrogen atom or an alkyl, alkoxy or aryl group, the alkyl and alkoxy groups being optionally substituted by halogen and the aryl group being optionally substituted by halogen and/or alkyl.

Ring-substituted (o-naphthoquinone 2-diazide)-4-sulfonic acids (diazo compounds $D_1$) are compounds of the formula IV

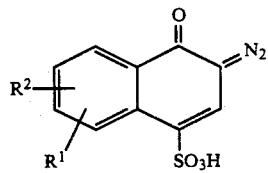

(IV)

in which $R^1$ and $R^2$ are identical or different and are a hydrogen atom, an alkyl, alkoxy or alkylmercapto group whose carbon chains can be interrupted by oxygen atoms (i.e., CH_2 groups can be replaced by ethereal —O—), an acylamino, alkoxycarbonyl, N-alkylsulfamoyl or N,N-dialkylsulfamoyl group, with the proviso that $R^1$ and $R^2$ are not hydrogen at the same time.

Preferred compounds of the formula IV are those in which
$R^1$ is hydrogen and
$R^2$ is an alkyl, alkyl ether or alkylmercapto group whose carbon chains can be interrupted by ethereal oxygen atoms.

Particularly preferred is 7-methoxy-(1,2-naphthoquinone 2-diazide)-4-sulfonic acid.

Particularly suitable diazo compounds $D_2$ are (o-naphthoquinone 2-diazide)-4- and -5-sulfonic acids of the formula V

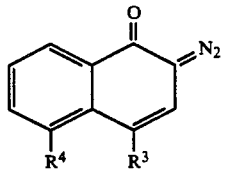

(V)

in which $R^3$ and $R^4$ are different and are a hydrogen atom or a sulfo group.

The compounds $D_0$ are non-radiation-sensitive organic acids of the formula VI $$R^5-Z-OH \qquad (VI)$$

in which
$R^5$ is a saturated or unsaturated, straight-chain or branched $(C_1-C_{25})$alkyl, $(C_1-C_{25})$alkoxy or $(C_1-C_{25})$alkylmercapto group whose carbon chains can be interrupted by oxygen atoms or which can be substituted by halogen or aromatics, an optionally halogen- or alkyl-substituted $(C_6-C_{14})$aryl, $(C_6-C_{14})$aralkyl or $(C_6-C_{14})$cycloalkyl group and
Z is a carbonyl or sulfonyl group.

Some particularly suitable aromatic polyhydroxyl compounds of the formula I are enumerated below:
polyhydroxybenzenes, such as 1,3-dihydroxybenzene, 1,4-dihydroxybenzene, 1,2,3-trihydroxybenzene, 1,2,4-trihydroxybenzene, 1,3,5-trihydroxybenzene, etc.;
dihydroxybenzophenones, such as 2,2'-dihydroxybenzophenone, 2,3'-dihydroxybenzophenone, 2,4-dihydroxybenzophenone, 2,4'-dihydroxybenzophenone, 2,5-dihydroxybenzophenone, 3,3'-dihydroxybenzophenone, 4,4'-dihydroxybenzophenone, etc.;
trihydroxybenzophenones, such as 2,6,2'-trihydroxybenzophenone, 2,3,4-trihydroxybenzophenone, 2,4,4'-trihydroxybenzophenone, 2,4,6-trihydroxybenzophenone, 3,4,5-trihydroxybenzophenone, etc.;
tetrahydroxybenzophenones, such as 2,3,4,2'-tetrahydroxybenzophenone, 2,4,2',4,-tetrahydroxybenzophenone, 2,4,2',6'-tetrahydroxybenzophenone, 2,5,2',6,-tetrahydroxybenzophenone, 2,3,4,4'-tetrahydroxybenzophenone, 2,4,3',4'-tetrahydroxybenzophenone, 2,4,6,3'-tetrahydroxybenzophenone, 2,4,6,4'-tetrahydroxybenzophenone, 3,4,3',4'-tetrahydroxybenzophenone, etc.;
pentahydroxybenzophenones, such as 2,3,4,2',4,-pentahydroxybenzophenone;
hexahydroxybenzophenones, such as 2,3,4,3',4',5'-hexahydroxybenzophenone;
di- and trihydroxyphenyl alkyl ketones, such as 2,4-dihydroxyphenyl alkyl ketone, 2,5-dihydroxyphenyl alkyl ketone, 3,4-dihydroxyphenyl alkyl ketone, 3,5-dihydroxyphenyl alkyl ketone, 2,3,4-trihydroxyphenyl alkyl ketone, 3,4,5-trihydroxyphenyl alkyl ketone, 2,4,6-trihydroxyphenyl alkyl ketone, etc., where the alkyl part preferably denotes $(C_1-C_{12})$alkyl groups which are optionally branched, such as methyl, ethyl, butyl, n-hexyl, heptyl, decyl, dodecyl, etc.;
di- and trihydroxyphenyl aralkyl ketones, di-, tri- and tetrahydroxydiphenyls, dihydroxydiphenyl ethers, dihydroxydibenzyl ethers and di(hydroxydiphenyl)alkanes whose alkane part is preferably derived from lower alkanes, such as methane, ethane, propane, etc.

The alkane part may also be substituted, a particularly preferred compound of this type being 2-ethoxyethyl 4,4-bis(4-hydroxyphenyl)valerate;

hydroxybenzoic acids and their esters, such as di- and trihydroxybenzoic acid, alkyl di- and trihydroxybenzoates, where the alkyl group preferably possesses 1 to 12 carbon atoms, and particularly 1 to 8 carbon atoms, in particular n-butyl 2,4-, 2,5-, 3,4- and 3,5-dihydroxybenzoates,2,4,4-trimethylpentyl-2,4-dihydroxybenzoates, etc.; phenyl di- and trihydroxybenzoates, di-, tri- and tetrahydroxydiphenyl sulfides, such as 4,4,-dihydroxydiphenyl sulfide; dihydroxydiphenyl sulfones, di- and trihydroxyphenyl naphthyl ketones, such as 2,3,4-trihydroxyphenyl 1-naphthyl ketone and similar compounds.

The compounds of the formula I in which at least one $R_b$ group is a halogen atom or a lower alkyl group include, for example, 2,4-dihydroxy-3,5-dibromobenzophenone, 5-bromo-2,4-dihydroxybenzoic acid and its esters, 2,4,2'4'-tetrahydroxy-3,5,3',5'-tetrabromodiphenyl, 4,4'-dihydroxy-2,2'-dimethyl-5,5'-di(tert-butyl)-diphenyl, 4,4'-dihydroxy-2,2'-dimethyl-5,5'-di(tert-butyl)diphenyl sulfide, 2,4,2',4'-tetrahydroxy-3,5,3',5'-tetrabromodiphenyl sulfone and the like.

The tri-, tetra- and hexahydroxybenzophenones and the trihydroxyphenyl alkyl ketones are preferably used as aromatic polyhydroxyl compounds of the formula I.

The phenol compounds of the formula II preferably include the following compounds: dihydroxynaphthalenes, such as 1,2-, 1,4-, 1,5-, 1,6-, 1,7-, 1,8-, 2,3-, 2,6- and 2,7-dihydroxynaphthalene; dihydroxydinaphthylmethanes, such as 2,2',-dihydroxydinaphthylmethane.

The dihydroxynaphthalenes are preferably used. In this connection, the hydroxyl groups of the dihydroxynaphthalenes may either be all on one ring or, advantageously, on both nuclei of the naphthalene molecule.

Compounds of the formula III are preferably bis(3-benzoyl-4,5,6-trihydroxyphenyl)methane, bis(3-acetyl4,5,6-trihydroxyphenyl)methane, bis(3-propionyl-4,5,6-trihydroxyphenyl)methane, bis(3-butyryl-4,5,6-trihydroxyphenyl)methane, bis(3-hexanoyl-4,5,6-trihydroxyphenyl)methane,bis(3-heptanoyl-4,5,6-trihydroxyphenyl)methane, bis(3-decanoyl-4,5,6-trihydroxyphenyl)methane and bis(3-octadecanoyl-4,5,6,-trihydroxyphenyl)methane.

The esterification is in general carried out with suitable activated derivatives of (naphthoquinone diazide)-sulfonic acids, especially the acid halides, in particular the acid chlorides. Suitable derivatives of diazo compounds D of the formula IV are, for example, (A) (5-methoxy-1,2-naphthoquinone 2-diazide)-4-sulfonyl chloride, (B) (6-methoxy-1,2-naphthoquinone2-diazide)-4-sulfonyl chloride, (C) (7-methoxy-1,2-naphthoquinone 2-diazide)-4-sulfonyl chloride, (D) (8-methoxy-1,2-naphthoquinone 2-diazide)-4-sulfonyl chloride, (E) (5-methyl-1,2-naphthoquinone 2-diazide)-4-sulfonyl chloride, (F) (6,7-dimethyl-1,2-naphthoquinone 2-diazide)-4-sulfonyl chloride, (G) (7-acetylamino-1,2-naphthoquinone 2-diazide)-4-sulfonyl chloride, (H) (7-methylmercapto1,2-naphthoquinone 2-diazide)-4-sulfonyl chloride, (I) (7-dimethylsulfamoyl-1,2-naphthoquinone 2-diazide)-4-sulfonyl chloride, (J) (6-bromo-1,2-naphthoquinone 2-diazide)-4-sulfonylchloride, (K) (6-methoxycarbonyl-1,2naphthoquinone 2-diazide)-4-sulfonyl chloride.

Particularly preferred is (7-methoxy-1,2naphthoquinone 2-diazide)-4-sulfonyl chloride, whose preparation is specified in DE-A 38 37 500 and in the German Patent Applications P 39 26 774.1 and p 39 26 776.8 (corresponding to U.S. Ser. Nos. 07/564,643 and 07/564,612) which are not previously published and which are incorporated herein by reference.

Suitable derivatives of diazo compounds $D_2$ of the formula V are, for example, (L) (o-naphthoquinone 2-diazide)-4-sulfonyl chloride and (M) (o-naphthoquinone 2-diazide)-5-sulfonyl chloride.

Suitable derivatives of organic, non-radiation-sensitive acids of the formula VI are, for example, acyl halides, such as (N) acetyl, propionyl, butyryl, isobutyryl, valeryl, isovaleryl, pivaloyl, caproyl, capryloyl, caprinoyl chloride, (O) lauroyl, myristoyl, palmitoyl chloride, (P) stearoyl, cerotoyl, (=hexacosanoyl), acryloyl, oleoyl, linoloyl, docos-11-enoyl, tetracos-15c-enoyl chloride, (Q) benzoyl and naphthoyl chloride, (R) 2-ethylhexanoyl, 7-methyloctanoyl, 7,7-dimethyloctanoyl chloride (S) 2-chloropropionyl, 4-chlorobutyryl chloride, (ST) methoxyacetyl chloride, methyl chloroformate, ethyl chloroformate, propyl chloroformate, butyl chloroformate, (T) 2-ethylhexyl chloroformate, octyl chloroformate, hexadecyl chloroformate, methoxyethyl chloroformate, alkanesulfonyl halides, such as (U) methane-, ethane-, propane-, n-butane- and dodecanesulfonyl chloride; arylsulfonyl halides, such as (V) benzene-, (W) toluene - and naphthalenesulfonyl chloride.

Preferred are alkanoyl and alkanesulfonyl halides containing 1 to 16 carbon atoms and aroyl and arylsulfonyl halides containing 6 to 8 carbon atoms. The acid halides may optionally be substituted.

The halides of the acids of the formulae V and VI are prepared analogously to processes known in the literature. Compared with the esters prepared only with the diazo compound $D_1$ or the diazo compound $D_2$, the mixed esters according to the invention are notable for a surprisingly higher solubility in the solvents or solvent mixtures standard for radiation-sensitive mixtures. The lithographic properties of the mixed esters according to the invention, particularly those which are obtained by condensation of aromatic polyhydroxyl compounds with a mixture of the diazo compounds $D_1$ and $D_2$ in a molar ratio of between about 1.5:1 and 9:1, are better than those of the known esters based on (o-naphthoquinone 2-diazide)-4- and -5-sulfonic acid. Because of their beneficial absorption characteristics, the novel mixed esters are particularly well suited both for i-line and for g-line exposure.

The invention also relates to a process for the preparation of the mixed esters according to the invention, in which one of the aromatic polyhydroxyl compounds of the formulae I to III is condensed in a polar organic solvent with the mixture composed of the (o-naphthoquinone 2-diazide)-4-sulfonyl chloride ($D_1$) and the (o-naphthoquinone 2-diazide)-4- or -5-sulfonyl chloride ($D_2$) and/or the non-radiation-sensitive organic acid chloride ($D_0$) in the presence of a basic compound, the $D_1$:($D_2$ and/or $D_0$) molar ratio in the mixture being between about 0.1:1 and 39:1, preferably between about 0.25:1 and 19:1, in particular between about 1.5:1 and 9:1, and in which the condensation products are isolated and optionally purified. For example, 1 mol of 2,3,4,4'-tetrahydroxybenzophenone is condensed with a mixture of 3.6 mol of sulfonyl chloride $D_1$ and 0.4 mol of sulfonyl chloride $D_2$ in a mixing ratio of 9:1. The radiation-sensitive compound obtained comprises units of the formula VII

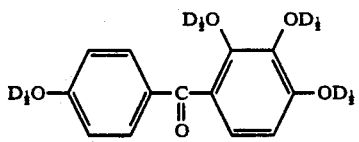

$$\text{(VII)}$$

in which $D_1$ and $D_2$ are, each case independently of one another, an (o-naphthoquinone 2-diazide)-4-sulfonyl group of the compound $D_1$ or an (o-naphthoquinone 2-diazide)-4- or -5-sulfonyl group of the compound $D_2$.

The aromatic polyhydroxyl compound of the formulae I to III is preferably reacted with about the stoichiometric amount of the mixture of the diazosulfonyl chlorides $D_1$ and $D_2$ or the diazosulfonyl chloride $D_1$ and the organic acid chloride $D_0$. The polyhydroxyl compounds do not, however, have to be fully esterified; smaller than stoichiometric amounts of diazosulfonyl chloride $D_1$, $D_2$ or acid chloride $D_0$ may also be used for the condensation with the polyhydroxyl compound.

The total amount of the sulfonyl chlorides $D_1$ and $D_2$, and/or $D_0$ respectively, which is reacted with the polyhydroxyl compounds, should be so dimensioned that a radiation-sensitive compound is obtained which ensures an adequate solubility of the radiation-sensitive mixture in the alkaline medium after exposure.

PREPARATION OF THE RADIATION-SENSITIVE CONDENSATION PRODUCTS

Processes for the preparation of radiation-sensitive compounds based on naphthoquinone diazides are described, for example, in U.S. Pat. Nos. 3,046,118; 3,106,645; 4,397,937; and also in DE-A 38 37 500, 39 26 774 and 39 26 776.

The radiation-sensitive compounds according to the invention are prepared by condensation of the (o-naphthoquinone 2-diazide)sulfonyl chlorides $D_1$ and $D_2$, and/or of the non-radiation-sensitive organic acid chloride $D_0$ with the polyhydroxyl compounds of the formulae I to III in the presence of an acidbinding substance. The radiation-sensitive compounds obtained in this way optionally may also be purified.

Suitable solvents for carrying out the condensation reaction are, for example, acetone, dioxane, tetrahydrofuran, acetonitrile, methylene chloride, pyridine, etc.

The acid-binding substance may be inorganic, such as sodium carbonate or sodium hydrogen carbonate, or organic, for example the sodium salt of a weak organic acid, such as sodium acetate; a tertiary amine, such as triethylamine, N-methylmorpholine or 1,4-diazobicyclo[2.2.2]octane (Dabcom ®); or pyridine or a pyridine derivative.

EXAMPLE 1

Preparation of a 2,3,4,4'-tetrahydroxybenzophenone condensed with the (o-naphthoquinone 2-diazide)sulfonyl chlorides $D_1$ and $D_2$ in the molar ratio 4.54:1

53.01 g (0.2155 mol) of 2,3,4,4'-tetrahydroxybenzophenone and 178.43 g (1.767 mol) of N-methylmorpholine are dissolved in 4.095 l acetonitrile. A total of 41.81 g (0.1557 mol) of solid (o-naphthoquinone 2-diazide)-5-sulfonyl chloride ($D_2$) is introduced while stirring in three portions of, in each case, 18.68 g, 13.40 g and 9.76 g at time intervals of 2 min. into the orange solution cooled to approximately 22 to 23° C. Stirring of the brownish orange solution is continued for a further 79 min. Then a total of 211.19 g (0.7075 mol) of (7-methoxy-1,2-naphthoquinone 2-diazide)-4-sulfonyl chloride ($D_1$) is added in the same way in three portions of 129.9 g, 52.36 g and 28.93 g in time intervals of 10 min. After adding the second portion of the sulfonyl chloride $D_1$, the deposition of a fine crystalline precipitate starts, and after adding the third portion, deposition of a brown viscous oil begins. Stirring of the reaction mixture is continued for a further 3 h at 25° to 28° C., and then the liquid reaction phase is decanted. The brown viscous oil adhering to the inside wall of the reaction vessel is dissolved in 3 l of acetone and added to the decanted reaction solution. The combined darkbrown solutions are then added dropwise to 43.86 l of a mixture of water and 37%-strength hydrochloric acid (50:1) while stirring. After standing for 24 h at 22° to 23° C., the light-yellow suspension is filtered off by suction, rinsed with 1 l of water and expressed. The still filter-moist yellow reaction product is then dissolved in 6.456 l of acetone, treated with 21.6 g of active carbon and, after filtering off the active carbon, the clear orange filtrate obtained is added dropwise to 32.68 l of a mixture of water and 37%-strength aqueous hydrochloric acid (75:1) while stirring well in the course of approximately 90 min. Stirring of the light-yellow suspension is continued for a further 1 h at 22° to 23° C., after which it is allowed to stand for 24 h at this temperature. Then the light yellow reaction product is filtered off by suction, rinsed with 2 l of water, expressed well and dried for 24 h in a vacuum drying oven at 40° C. and 450 torr.

Yield: 252 g of light-yellow powder, equivalent to 92.13% of theory.

A number of condensation products according to the invention in which the molar ratios of the (o-naphthoquinone 2-diazide)sulfonyl chlorides $D_1$ and $D_2$ or of the (o-naphthoquinone 2-diazide)sulfonyl chloride $D_1$ and the non-radiation-sensitive organic acid chloride $D_0$ respectively were varied in accordance with Table 1, were prepared by the process described above.

For comparison purposes, condensation products of 2,3,4,4'-tetrahydroxybenzophenone and only one of the following (o-naphthoquinone 2-diazide)sulfonyl chlorides $D_1$ and $D_2$ in a molar ratio of 1:4 were prepared: ($D_1$) (7-methoxy-1,2-naphthoquinone 2-diazide)-4-sulfonyl chloride and ($D_2$) (o-naphthoquinone 2-diazide)-4- or -5-sulfonyl chloride

TABLE 1

| | POLYHYDROXYL COMPOUNDS | | | | | ORGANIC ACID HALIDES | | | | | | MOLAR RATIO | | |
|---|---|---|---|---|---|---|---|---|---|---|---|---|---|---|
| | EBHPV[1]) | TOB[2]) | THB[3]) | PHB[4]) | HHB[5]) | PAH[6]) | | | | NPAH[7] | | | | |
| No. | | | MOL | | | $D_1$ | Mol$_{D_1}$ | $D_2$ | Mol$_{D_2}$ | $D_0$ | Mol$_{D_0}$ | $D_1/D_2$ | $D_1/D_0$ | DOE[8]) (%) |
| 1 | 1 | | | | | C | 0.4 | M | 3.6 | | | 0.11:1 | | 100 |
| 2 | | | | | 1 | C | 1.0 | M | 5.0 | | | 0.50:1 | | 100 |

TABLE 1-continued

| | POLYHYDROXYL COMPOUNDS | | | | | ORGANIC ACID HALIDES | | | | | | | | |
|---|---|---|---|---|---|---|---|---|---|---|---|---|---|---|
| | EBHPV[1]) | TOB[2]) | THB[3]) | PHB[4]) | HHB[5]) | PAH[6]) | | | | NPAH[7] | | MOLAR RATIO | | |
| No. | | | MOL | | | $D_1$ | $Mol_{D_1}$ | $D_2$ | $Mol_{D_2}$ | $D_0$ | $Mol_{D_0}$ | $D_1/D_2$ | $D_1/D_0$ | DOE[8]) (%) |
| 3 | | | | | 1 | C | 1.0 | M | 4.0 | | | 0.25:1 | | 100 |
| 4 | | 1 | | | | C | 0.6 | M | 2.4 | | | 0.25:1 | | 100 |
| 5 | | | 1 | | | C | 0.8 | M | 3.2 | | | 0.25:1 | | 100 |
| 5a | | | 1 | | | C | 1.0 | M | 3.0 | | | 0.33:1 | | 100 |
| 6 | | | 1 | | | C | 0.8 | M | 3.0 | | | 0.26:1 | | 95 |
| 7 | | | | 1 | | C | 1.0 | M | 3.0 | | | 0.33:1 | | 80 |
| 8 | | | | | 1 | C | 1.0 | M | 3.0 | | | 0.33:1 | | 66.66 |
| 9 | | 1 | | | | C | 2.0 | L | 2.0 | | | 1:00:1 | | 100 |
| 9a | | 1 | | | | C | 3.5 | L | 0.5 | | | 7.00:1 | | 100 |
| 10 | | 1 | | | | D | 1.8 | M | 1.2 | | | 1.50:1 | | 100 |
| 11 | | | | 1 | | A | 1.8 | M | 1.2 | | | 1.50:1 | | 100 |
| 12 | | | 1 | | | C | 2.4 | M | 1.6 | | | 1.50:1 | | 100 |
| 13 | | 1 | | | | E | 1.8 | L | 0.9 | | | 2.00:1 | | 90 |
| 14 | | | 1 | | | B | 2.4 | M | 0.6 | | | 4.00:1 | | 100 |
| 15 | | | 1 | | | C | 3.3 | M | 0.7 | | | 4.71:1 | | 100 |
| 16 | | | | | 1 | C | 5.0 | | | P | 1.0 | | 5.00:1 | 100 |
| 17 | | | | 1 | | C | 5.0 | | | T | 1.0 | | 5.00:1 | 100 |
| 18 | | | | 1 | | C | 5.0 | | | R | 1.0 | | 5.00:1 | 100 |
| 19 | | | | 1 | | C | 5.0 | | | U | 1.0 | | 5.00:1 | 100 |
| 20 | 1 | | | | | C | 1.75 | | | Q | 1.25 | | 7.00:1 | 100 |
| 21 | | 1 | | | | K | 2.4 | | | O | 0.3 | | 8.00:1 | 90 |
| 22 | | | 1 | | | C | 3.4 | M | 0.4 | | | 8.50:1 | | 95 |
| 23 | 1 | | | | | I | 1.7 | | | W | 0.2 | | 8.50:1 | 95 |
| 24 | | 1 | | | | G | 2.7 | | | N | 0.3 | | 9.00:1 | 100 |
| 25 | | 1 | | | | C | 2.7 | L | 0.3 | | | | 9.00:1 | 100 |
| 26 | | 1 | | | | C | 2.7 | M | 0.3 | | | | 9.00:1 | 100 |
| 27 | | | | 1 | | C | 4.0 | | | ST | 0.4 | | 10.0:1 | 88 |
| 28 | | 1 | | | | C | 3.75 | M | 0.25 | | | 15.0:1 | | 100 |
| 29 | 1 | | | | | C | 1.9 | | | S | 0.1 | | 19.0:1 | 100 |
| 30 | | 1 | | | | | | M | 4.0 | | | Comp. | | 100 |
| 31 | | 1 | | | | | | L | 4.0 | | | Comp. | | 100 |
| 32 | | 1 | | | | C | 4.0 | | | | | Comp. | | 100 |
| 33 | | | | 1 | | C | 6.0 | | | | | Comp. | | 100 |
| 34 | | | | | 1 | | | M | 6.0 | | | Comp. | | 100 |
| 35 | 1 | | | | | | | M | 3.0 | | | Comp. | | 100 |
| 36 | | 1 | | | | | | M | 4.0 | | | Comp. | | 95 |

[1])Ethoxyethyl 4,4-bis(4-hydroxyphenyl)valerate (mol. wt.: 258)
[2])2,3,4-trihydroxybenzophenone (mol. wt.: 230)
[3])2,3,4,4'-tetrahydroxybenzophenone (mol. wt.: 246)
[4])2,2',3,4,4'-pentahydroxybenzophenone (mol. wt.: 262)
[5])2,3,3',4,4',5'-hexahydroxybenzophenone (mol. wt: 278)
[6])Photosensitive acid halide
[7])Nonphotosensitive acid halide
[8])Degree of esterification

EXAMPLE 2

The solubility of the photoactive compounds was determined in a 26%-strength by weight solution of a novolak in methoxypropanol acetate (MPA) since the solutions produced correspond much more to the reality of a photoresist mixture than solutions of the compounds according to the invention in pure MPA. In doing this, the photoactive compounds were added to the novolak solution in portions until complete solution no longer occurred (in the comparison examples) or the addition was discontinued at particular percentage contents of the solutions despite the continued existence of solubility (in the case of the compounds according to the invention). In all cases it was possible to observe a markedly improved solubility of the compounds according to the invention compared with corresponding comparison compounds (see Table 2).

TABLE 2

| Compounds No. | Solubility L (%) |
|---|---|
| 4 | >7.0 |
| 35 (comparison) | 2.4 < L < 4.8 |
| 5 | >4.8 |
| 5a | >7.0 |
| 9a | >4.8 |
| 15 | >7.0 |
| 30 (comparison) | <2.4 |

TABLE 2-continued

| Compounds No. | Solubility L (%) |
|---|---|
| 32 (comparison) | <2.4 |
| 6 | >11.1 |
| 36 (comparison) | 9.1 < L < 10.1 |
| 16 | 22.3 < L < 24.8 |
| 17 | >28.8 |
| 18 | >37.5 |
| 19 | 10.1 < L < 12.9 |
| 33 (comparison) | <7.3 |
| 34 (comparison) | <4.4 |

What is claimed is:

1. A radiation-sensitive ester which is the condensation product of
   (a) a compound containing two to six aromatic hydroxyl groups,
   (b) a compound $D_1$ which is a ring-substituted (o-naphthoquinone 2-diazide)-4-sulfonic acid, and
   (c) a compound $D_2$ which is an o-naphthoquinone 2-diazide)-4-sulfonic acid which is not further substituted or an (o-naphthoquinone 2-diazide)-5-sulfonic acid which is not further substituted,
   wherein the molar ratio (b):(c) is between about 0.0:1 and 39:1.

2. A radiation-sensitive ester as claimed in claim 1, wherein said compound (a) is an aromatic polyhydroxyl compound corresponding to the formula I

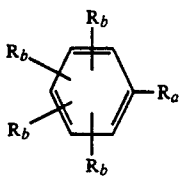
(I)

where $R_a = $ —H, -X-$R_c$ or

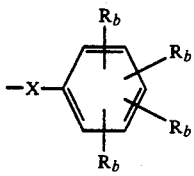

in which $R_b$ is a hydrogen or halogen atom, or a hydroxyl or ($C_1$-$C_6$)alkyl group, with the proviso that at least two and not more than six of the $R_b$ groups are hydroxyl groups and the radicals $R_b$ are identical to, or different from, one another, X is a single bond, —O—, —S—, —SO$_2$—, —CO1', —CO—CH$_2$—, —CO—CH$_2$—CH$_2$—, —CO—CH$_2$—CO—, —CO—CH$_2$—CH$_2$—CO—, —CO—O—, —CO—O—CH$_2$—, —CO—O—CH$_2$—CH$_2$—, —CH$_2$—CO—O—CH$_2$—, —CH$_2$—CO—O—CH$_2$—CH$_2$—, —CH$_2$—, —CH$_2$—CH$_2$—, —(CH$_2$)$_3$, —C(CH$_3$)$_2$—, —C(CF$_3$)$_2$—,

—CH—CH$_2$—Y, —CH—CH$_2$—CH$_2$—Y,
  |                |

—C(CH$_3$)—CH$_2$—Y, or —C(CH$_3$)—CH$_2$—CH$_2$—Y,
  |                          | where CH$_2$ groups can be replaced by —O—, and hydrogen atoms can be replaced by substituents such as alkyl or aryl.

Y is a hydrogen atom or an alkoxy, carboxyl, alkoxycarbonyl, alkoxyalkoxycarbonyl or aryl group, the alkoxy, alkoxycarbonyl and alkoxyalkoxycarbonyl groups being optionally substituted by halogen or aryl and the aryl group being optionally substituted by alkyl, and $R_c$ is a hydrogen atom or an optionally halogen-substituted alkyl or aryl group.

3. A radiation-sensitive ester as claimed in claim 1, wherein said compound (a) corresponds to the formula II

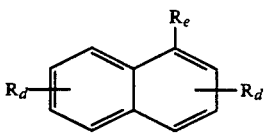
(II)

in which $R_c$ is a hydrogen atom or an optionally halogen- or alkyl-substituted 1-naphthylmethyl group

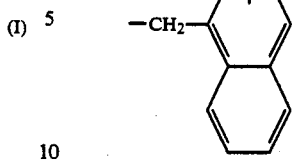

where $R_d$ is a hydrogen atom or a hydroxyl group, with the proviso that at least two of the $R_d$ groups are hydroxyl groups.

4. A radiation-sensitive ester as claimed in claim 1, wherein said compound (a) corresponds to the formula III

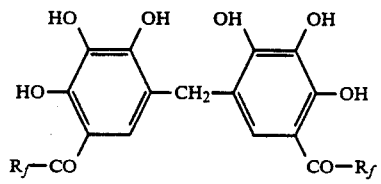
(III)

in which $R_f$ is a hydrogen atom or an alkyl, alkoxy or aryl group, the alkyl and alkoxy groups being optionally substituted by halogen and the aryl group being optionally substituted by halogen and/or alkyl.

5. A radiation-sensitive ester as claimed in claim 1, wherein said ring-substituted (o-naphthoquinone 2-diazide)-4-sulfonic acid compound D corresponds to the formula IV

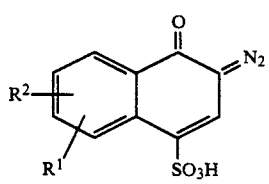
(IV)

in which $R^1$ and $R^2$ are identical or different and are a hydrogen atom, an alkyl, alkoxy or alkylmercapto group whose carbon chains can be interrupted by oxygen atoms, an acylamino, alkoxycarbonyl, N-alkylsulfamoyl or N,N-dialkylsulfamoyl group, with the proviso that $R^1$ and $R^2$ are not hydrogen at the same time.

6. A radiation-sensitive ester as claimed in claim 5, wherein $R^1$ is a hydrogen atom and $R^2$ is an alkyl, alkoxy or alkylmercapto group whose carbon chains can be interrupted by oxygen atoms.

7. A radiation-sensitive ester as claimed in claim 6, wherein $R^1$ is a hydrogen atom and $R^2$ is a 7-methoxy group.

8. A radiation-sensitive ester as claimed in claim 1, wherein said (o-naphthoquinone 2-diazide)-4- or -5-sulfonic acid compound $D_2$ corresponds to the formula V

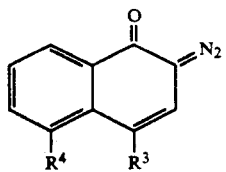 (V)

in which

R³ and R⁴ are different and are a hydrogen atom or a sulfonyl group.

9. A radiation-sensitive ester as claimed in claim 1, wherein (c) further comprises a non-radiation-sensitive organic acid.

10. A radiation-sensitive ester as claimed in claim 1, wherein (c) further comprises a non-radiation-sensitive organic acid compound $D_0$ of the formula VI $$R^5\text{-}Z\text{—OH} \qquad \text{(VI)}$$

in which

R⁵ is a saturated or unsaturated, straight-chain or branched ($C_1$-$C_{25}$)alkyl, ($C_1$-$C_{25}$)alkoxy or ($C_1$-$C_{25}$)alkylmercapto group whose carbon chains can be interrupted by oxygen atoms or which can be substituted, an optionally substituted ($C_6$-$C_{14}$)aryl, ($C_6$-$C_{14}$)aralkyl or ($C_6$-$C_{14}$)cycloalkyl group, and Z is a carbonyl or sulfonyl group.

11. A radiation-sensitive ester as claimed in claim 2, wherein said aromatic polyhydroxyl compound is a tri-, tetra-, penta- or hexahydroxybenzophenone or a trihydroxyphenyl alkyl ketone.

12. A radiation-sensitive ester as claimed in claim 1, wherein the molar ratio (b):(c) is between about 0.25:1 and 19:1.

13. A radiation-sensitive ester as claimed in claim 12, wherein said molar ratio is between about 1.5:1 and 9:1.

14. A radiation-sensitive ester as claimed in claim 1, wherein the condensation product is fully esterified.

15. A radiation-sensitive ester as claimed in claim 1, wherein (c) comprises an (o-naphthoquinone 2-diazide)-5-sulfonic acid which is not further substituted.

16. A radiation-sensitive composition as claimed in claim 1, wherein (b) comprises 5, 6, or 7-methoxy-(1,2-naphthoquinone 2-diazide)-4-sulfonic acid.

17. A process for producing a radiation-sensitive ester which is the condensation product of
(a) a compound containing two to six aromatic hydroxyl groups,
(b) a compound $D_1$ which is a ring-substituted (o-naphthoquinone 2-diazide)-4-sulfonic acid, and
(c) a compound $D_2$ which is an (o-naphthoquinone 2-diazide)-4-sulfonic acid which is not further substituted or an (o-naphthoquinone 2-diazide)-5-sulfonic acid which is not further substituted,
wherein the molar ratio (b):(c) is between about 0.1:1 and 39.1,
which comprises the steps of condensing compound (a) in a polar organic solvent with a mixture of compounds (b) and (c) in the presence of a base, the molar ratio (b):(c) being between about 0.1:1 and 39:1, to form a condensation product, and isolating said condensation product.

18. A process as claimed in claim 17, wherein said molar ratio is between about 0.25:1 and 19:1.

19. A process as claimed in claim 18, wherein said molar ratio is between about 1.5:1 and 9:1.

20. A process as claimed in claim 17, further comprising the step of purifying said condensation product after said isolation step.

21. A process as claimed in claim 17, wherein said compound (a) is reacted with about the stoichiometric amount of said mixture.

22. A process as claimed in claim 17, wherein (c) further comprises a non-radiation-sensitive organic acid.

* * * * *

UNITED STATES PATENT AND TRADEMARK OFFICE
CERTIFICATE OF CORRECTION

PATENT NO. : 5,268,252
DATED : December 7, 1993
INVENTOR(S) : SCHELER et al.

It is certified that error appears in the above-indentified patent and that said Letters Patent is hereby corrected as shown below:

Column 12, line 67, Claim 1, contains a typographical error wherein "0.0" should read --0.1--;

Column 13, line 29, Claim 2, contains a typographical error wherein "——CO1——" should read -- ——CO—— --;

Column 13, line 67, Claim 3, contains a typographical error wherein "$R_C$" should read --$R_e$--;

Column 14, line 37, Claim 4, contains a typographical error wherein "D" should read --$D_l$--.

Signed and Sealed this

Twenty-eighth Day of June, 1994

Attest:

BRUCE LEHMAN

Attesting Officer        Commissioner of Patents and Trademarks